United States Patent [19]

Swedo

[11] 4,426,313

[45] Jan. 17, 1984

[54] PREPARATION OF SURFACTANTS BY SULFONATING DERIVATIVES OF DEPOLYMERIZED COAL

[75] Inventor: Raymond J. Swedo, Mount Prospect, Ill.

[73] Assignee: UOP Inc., Des Plaines, Ill.

[21] Appl. No.: 435,135

[22] Filed: Oct. 18, 1982

[51] Int. Cl.$^3$ .............................................. B01F 17/12
[52] U.S. Cl. ......................................... 252/353; 208/9
[58] Field of Search .................... 252/353; 260/505 C, 260/505 R; 208/8 R, 8 LE, 9, 10

[56] References Cited

U.S. PATENT DOCUMENTS 2,807,589  9/1957  Mitchell et al. ...................... 252/353
2,940,936  6/1960  Fike ..................................... 252/353

OTHER PUBLICATIONS

Ouchi et al., *Fuel,* "Catalysts for the Depolymerization of Mature Coals," 52, Apr. (1973), pp. 156–157.

*Primary Examiner*—Richard D. Lovering
*Assistant Examiner*—Anne Brookes
*Attorney, Agent, or Firm*—James R. Hoatson, Jr.; Raymond H. Nelson; William H. Page, II

[57] ABSTRACT

Surfactants or surface active agents may be obtained by treating the product obtained from the boron trifluoride etherate catalyzed depolymerization of coal with a sulfonating agent such as sulfur trioxide and thereafter neutralizing the sulfonated product with a basic compound such as sodium hydroxide to obtain a sodium sulfonated derivative of the depolymerized coal product.

7 Claims, No Drawings

000# PREPARATION OF SURFACTANTS BY SULFONATING DERIVATIVES OF DEPOLYMERIZED COAL

BACKGROUND OF THE INVENTION

Surfactants or surface active agents are compounds which effect, usually in the form of reducing, surface tension between two phases usually when dissolved in water or water solutions. While soap is considered a surface active agent, the usual surfactant comprises an organic derivative such as a sodium salt of high molecular weight alkyl sulfates or sulfonates. The surfactants are used as detergents, wetting agents, penetrants, spreaders, dispersing agents or foaming agents. Therefore, such compounds find a wide variety of uses in many commercial applications. One such application is in enhanced oil recovery where after obtaining as much petroleum as possible due to natural sources such as pressure either by the petroleum itself or by the presence of gases, the residual petroleum still present in the reservoir is recovered by a secondary process. The secondary process usually involves forcing water into the reservoir to provide the pressure necessary to force the petroleum from the reservoir to the surface. However, at some point in the recovery of petroleum, a state is reached in which it is more costly to use the water pumped into the reservoir relative to the amount of oil which is recovered by this method. It is therefore necessary to effect the recovery of any petroleum which may still be present in the reservoir, either in a pool or by being trapped in interstices of relatively porous rock, by a tertiary method. One particular means for effecting the tertiary method is by utilizing surfactants as a plug, whereby the oil or petroleum which is present in the reservoir may be recovered by injecting an aqueous fluid containing a surfactant or a combination of surfactants along with other compounds into the reservoir. The use of surfactants in this system is necessary inasmuch as water alone does not displace the petroleum with a relatively high degree of efficiency. This occurs due to the fact that water and oil are relatively immiscible and, in addition, the interfacial tension between water and oil is relatively high. The use of surfactants will lower or reduce the interfacial tension between the water and the oil, thus reducing the force which retains the oil which has been trapped in capillaries, and will thus enable the oil to be recovered in a more efficient manner.

As will hereinafter be shown in greater detail, it has now been discovered that compounds which possess desirable surfactant properties may be prepared by utilizing, as one component thereof, the product resulting from the depolymerization of coal. Coal is basically a large cross-linked, complex natural polymer which can be depolymerized to yield simpler units. The depolymerization of coal may be effected by treating the coal with an organic solvent in the presence of certain catalysts to cleave the polymeric bonds in the coal structure and thus produce smaller molecules. The organic reagents or solvents which had been employed will comprise mono- or polyhydroxy aromatic compounds, while the catalysts which are employed will include Friedel Crafts catalysts as well as some acidic catalysts.

The depolymerization of the coal may be carried out by treating the coal at an elevated temperature in the presence of the organic solvent and the catalyst. After allowing the depolymerization reaction to continue for a predetermined period of time, the acid catalyst may then be neutralized by treatment with a basic compound such as sodium hydroxide, potassium hydroxide, sodium carbonate, potassium carbonate, etc. The liquid and solids are separated by conventional means such as filtration, centrifugation, decantation, etc. The precipitates are then washed with organic solvents until a clear filtrate is obtained. The washings and decanted liquid are combined and subjected to distillation, preferably under reduced pressure, to yield a solid residue of depolymerized material. The depolymerized material may then be subjected to conventional refining processes to obtain the desired end product, which may then be used either per se or as components in further chemical reactions. The depolymerization of coal may be used as an alternative to other treatments of coal such as liquefaction which is usually accomplished by hydrogenation, solvent refining, etc.

It has now been discovered that the products which are obtained from the depolymerization of coal may be used directly, without any further process steps, to generate surfactants or surface active agents in a process which is hereinafter set forth in greater detail.

BRIEF SUMMARY OF THE INVENTION

This invention relates to a process for producing surfactant materials. More specifically, the invention is concerned with a process for preparing compounds which possess surfactant properties utilizing, as a source for one component of the compound, material which is abundant in nature and, due to its ready availability, will lower the overall cost of the desired product.

As was previously set forth, surfactants or surface active agents will find a wide variety of uses in industrial applications, while many surfactants must, of necessity, be colorless in nature due to a requirement for appearance. In some instances this appearance or product appearance is unimportant. Such applications would include the use of the surfactant in enhanced oil recovery or in lubrication.

It is therefore an object of this invention to provide a process for the preparation of surfactants.

A further object of this invention is found in a process for preparing surfactants utilizing readily available material as the source for one component thereof.

In one aspect an embodiment of this invention resides in a process for the preparation of a surfactant which comprises treating the product obtained from the depolymerization of coal with a solfonating agent at sulfonation conditions, neutralizing the sulfonated product and recovering the resultant surfactant.

A specific embodiment of this invention resides in a process for the preparation of a surfactant which comprises treating the product obtained from the depolymerization of coal, which has been treated with phenol in the presence of boron trifluoride etherate, with a sulfonating agent comprising sulfur trioxide at a temperature in the range of from about ambient to about 50° C. and a pressure in the range of from about atmospheric to about 10 atmospheres, neutralizing the sulfonated product with sodium hydroxide and recovering the resultant surfactant.

Other objects and embodiments will be found in the following further detailed description of the invention.

DETAILED DESCRIPTION OF THE INVENTION

As hereinbefore set forth, the present invention is concerned with a process for the preparation of surfactants or surface active agents utilizing the product obtained by the depolymerization of coal as one of the starting materials. As was previously discussed, coal is readily abundant in nature and by utilizing the coal as the starting material for obtaining the desired product, it is possible to obtain the finished or end product in a more economical manner. The treatment of the coal whereby depolymerized products are obtained is accomplished by subjecting the coal to a depolymerization reaction utilizing, as a solvent for the reaction, a mono- or polyhydroxy aromatic hydrocarbon, said hydrocarbon being either monocyclic or polycyclic in configuration. Examples of the hydroxylated aromatic solvents which may be employed will include the monohydroxy compounds such as: phenol, 1-hydroxynaphthalene, 2-hydroxynaphthalene, 1-hydroxyanthracene, 2-hydroxyanthracene, 9-hydroxyanthracene, 1-hydroxyphenanthrene, 2hydroxyphenanthrene, 3-hydroxyphenanthrene, 2-hydroxybiphenyl, 3-hydroxybiphenyl, 4-hydroxybiphenyl, 4- hydroxydiphenylmethane, 3-hydroxyphenylether, 4-hydroxyphenylether, o-cresol, m-cresol, p-cresol, o-ethylphenyl, m-ethylphenol, p-ethylphenol, o-propylphenol, m-butylphenol, p-pentylphenol, o-hexylphenol, m-heptylphenol, p-octylphenol, o-nonylphenol, m-decylphenol, p-decylphenol, 1,2-dimethylphenol, 1,3-diethylphenol, 1,4-dipropylphenol, 1,5-butylphenol, 1,6-hexylphenol, 1-hydroxy-2-methylnaphthalene, 1-hydroxy-4-ethylnaphthalene, 1-hydroxy-5-octylnaphthalene, etc.; polyhydroxy aromatic compounds such as 1,2-dihydroxybenzene(pyrocatechin), 1,3-dihydroxybenzene(resorcinol), 1,4-dihydroxybenzene (hydroquinone), 2,3-dihydroxytoluene, 2,4-dihydroxytoluene(4-methylresorcinol), 2,5-dihydroxytoluene(toluhydroquinone), 2,6-dihydroxytoluene (2-methylresorcinol), 3,4-dihydroxytoluene(homocatechol), 1,2-dihydroxynaphthalene, 1,3-dihydroxynaphthalene, 1,4-dihydroxynaphthalene, 1,2-dihydroxyanthracene, 1,4-dihydroxyanthracene, 2,2'-dihydroxybiphenyl, 4,4'-dihydroxybiphenyl, 4,4'-dihydroxydiphenylmethane, 4,4'-dihydroxyphenylether, as well as the mono- or dialkylated derivatives thereof in which the alkyl groups will contain from 1 to 12 carbon atoms in the chain. The depolymerization reaction is also effected in the presence of an acidic catalyst which may comprise either a Friedel Crafts metal halide catalyst or an acidic catalyst. Examples of Friedel Crafts catalysts which may be employed will include aluminum chloride, ferric chloride, zinc chloride, etc., while acidic catalysts will include strong inorganic acids such as sulfuric acid, boron trifluoride, boron trifluoride etherate, hydrofluoric acid, hydrochloric acid, nitric acid, etc.

The depolymerization of the coal is effected at elevated temperatures which may range from about 100° up to about 250° C. or more, the depolymerization being effected for a period of time which may range from about 1 to about 24 hours or more in duration. Upon completion of the depolymerization reaction, the acid catalyst is then neutralized by treatment with a basic compound of the type hereinbefore set forth in greater detail. After neutralization has been effected, the solids are separated from the organic liquid portion of the reaction mixture by conventional means and thereafter the solids are washed, and after the washings have been combined with the liquid portion of the product, the unreacted solvents may be removed by conventional means such as distillation under a reduced pressure. Examples of solvents which may be used to wash the solid portion of the reaction mixture will include benzene, toluene, carbon tetrachloride, etc. If so desired, the residue may be further washed with water to remove any residual salts which may still be present and after drying to remove the water, the resulting product may then be sulfonated.

The sulfonation of the polymerized product may be accomplished by treating the alkylated product in an appropriate apparatus with a sulfonating agent such as liquid or gaseous sulfur trioxide, sulfuric acid, etc. in the presence of, if so desired, an organic solvent such as paraffins including pentane, hexane, heptane, etc. or cyclopentanes such as cyclopentane, methylcyclopentane, cyclohexane, etc. As one example of a sulfonation process, the depolymerized product may be charged to a reaction flask along with the desired solvent and thereafter liquid or gaseous sulfur trioxide is also charged to the reaction apparatus under a nitrogen blanket. The addition of the sulfonating agent to the depolymerized product may be effected at ambient temperature or temperatures slightly in excess of ambient, that is, up to about 50° C. over a relatively long period which may range from about 1 to about 10 hours or more in duration. Upon completion of the desired reaction period, the mixture may then be neutralized by the addition of an alkaline component such as ammonium hydroxide, sodium hydroxide, lithium hydroxide, magnesium hydroxide, calcium hydroxide, strontium hydroxide, ammonium carbonate, sodium carbonate, lithium carbonate, magnesium carbonate, calcium carbonate, strontium carbonate, etc. The addition of the alkaline component is effected until a pH in excess of 7 is reached, after which water is added to the reaction mixture along with an equal amount of an alcohol such as isopropyl alcohol. After thorough agitation, the mixture is then heated to a temperature in the range of from about 50° to about 75° C. for a predetermined period of time and is thereafter allowed to cool. The alkaline sulfate which separates upon cooling, is then removed by conventional means such as filtration, centrifugation, etc. and after the mixture is allowed to settle, it will separate into two layers. The lower aqueous/alcohol layer may then be extracted with an organic solvent such as hexane until the extracts are not colored. The upper organic layer along with the combined extract may then be washed with water which is added to the aqueous layer. Thereafter, the aqueous layer is allowed to evaporate to dryness or a drying means such as a steam bath is used to yield the neutralized sulfonated derivative of the depolymerized product.

It is also contemplated within the scope of this invention that the desired sulfonate may be prepared in a continuous type of operation. When such a type of operation is employed, a quantity of the depolymerized product which has been obtained in a manner hereinbefore set forth in greater detail is continuously charged to a sulfonation zone which is maintained at the proper operating conditions of temperature and pressure. In the sulfonation zone the depolymerized product is contacted with a sulfonating agent such as liquid or gaseous sulfur trioxide. After passage through this sulfonation zone for a predetermined period of time, the effluent is continuously withdrawn therefrom and passed to a second zone wherein it is contacted with a neutralizing agent such as sodium hydroxide. Upon completion of the neutralization reaction, the effluent from this zone is continuously withdrawn and treated in a manner similar to that hereinbefore set forth whereby the desired neutralized sulfonated derivative of the depolymerized product is separated and recovered.

The following examples are given for purposes of illustrating the process of the present invention. However, it is to be understood that these examples are merely illustrative in nature and that the present process is not necessarily limited thereto.

EXAMPLE I

A 10.0 gram sample of 100–200 mesh coal was mixed with 100 ml (107 grams) of phenol and 41 ml (18.1 grams) of boron trifluoride etherate in a 3-neck flask provided with a thermometer, a stirrer and a reflux condenser. The mixture was heated to a temperature of 145° C. and stirred for a period of 24 hours while maintaining the temperature in a range of from 145° and 150° C. At the end of this time, the mixture was cooled to a temperature of 70° C. and 20.0 grams (0.19 moles) of anhydrous sodium carbonate were added portion-wise during a period of 15 minutes. During the addition of the sodium carbonate, the mixture foamed. Upon completion of the addition of the neutralizing agent, the mixture was cooled to room temperature and the mixture was removed from the reaction vessel utilizing 600 ml of carbon tetrachloride. The mixture was then subjected to distillation under vacuum to remove the carbon tetrachloride, and a major portion of the unreacted phenol. The solids comprised a black tarry product.

EXAMPLE II

The black tarry residue which was obtained from Example I above after the distillation was treated with 200 ml of a 50 wt. % aqueous sodium hydroxide solution and thereafter the slurry was evaporated to dryness over a steam bath. The product was extracted several times with boiling pyridine until the extracts were colorless, and thereafter the extracts were filtered. The pyridine-in-soluble residue which remained from this treatment was washed with water until the washings were neutralized. After drying, the insoluble residue, amounting to 1.8 grams, was subjected to infra-red analysis, the spectrum matched that of the charged material of coal.

EXAMPLE III

The filtrate which was obtained from the pyridine extracts was subjected to distillation under vacuum to remove the pyridine and water, following which the resulting black solid residue was extracted with water for a period of 24 hours to remove any remaining phenol, sodium phenoxide and sodium hydroxide. The residual black solid was then further extracted for a period of 24 hours with acetone until the acteone extracts were colorless in nature. After removal of the water by drying, and after distilling off the acetone, a total of 37.1 grams of pyridine-soluble/acetone-soluble depolymerization products were obtained.

EXAMPLE IV

To prepare the desired surfactant, the 37.1 grams of the depolymerization products obtained from the above example were dissolved in 100 ml of methylene chloride in a 3-neck flask provided with a stirrer, a reflux condenser and a gas inlet tube. The solution was stirred while 14.7 grams (0.18 moles) of liquid sulfur trioxide was charged to a separate bubbler and introduced into the flask through the gas inlet tube as a 5–10% mixture in nitrogen at ambient temperature. The sulfur trioxide addition was accomplished over a period of 2 hours after which the reaction mixture was sparged with nitrogen for an additional period of 2 hours.

The resulting sulfonate mixture was neutralized to a pH of about 8 with approximately 30 ml of a 25 wt. % aqueous sodium hydroxide solution. Thereafter, the methylene chloride was removed from the reaction mixture by rotary evaporation at a temperature of 40° C. and the resulting aqueous solution was diluted with 30 ml of isopropyl alcohol. After warming the solution to a temperature of 80° C. for a short period of time, the solution was cooled in an ice bath to a temperature of 0° C. and maintained thereat for a period of 18 hours. The solution was then filtered to separate the sodium sulfate precipitate which had formed and the alcohol and water were removed from the filtrate by rotary evaporation at a temperature of 60° C. followed by drying under vacuum at 80° C. The yield of the desired surfactant comprised 49.6 grams of the sodium sulfonate salt of the pyridine-soluble/acetone-soluble depolymerization product.

EXAMPLE V

To illustrate the surfactant properties of the sodium sulfonate salt of the pyridine-soluble/acetone-soluble depolymerization product, the interfacial tension measurements of the surfactant were obtained by using the spinning drop technique as set forth in the article, "Adsorption at Interfaces" by J. L. Cayias, R. S. Schechter and W. H. Wade, ACS Symposium, Series No. 8, 1975, page 234. The solution which was used for the interfacial tension measurements comprised 0.70 gram per liter of the sodium sulfonate salt of the depolymerized product, 20 ml per liter of the alcohol of the type hereinafter set forth and 10 grams per liter of sodium chloride. This solution was measured against a series of pure hydrocarbons, the results of these tests being set forth in the following Table:

TABLE

SURFACTANT PROPERTIES OF SODIUM SULFONATE DERIVATIVE

| 0.70 g/l surfactant<br>10.00 g/l NaCl<br>20.00 ml/l alcohol<br>Alcohol | Surfactant Test Solution | |
|---|---|---|
| | n-Alkane | IFT (dynes/cm) |
| iso-butyl | 6 | $2.0 \times 10^{-0}$ |
| | 8 | $1.6 \times 10^{-0}$ |
| | 10 | $1.4 \times 10^{-0}$ |
| | 12 | $1.6 \times 10^{-0}$ |
| | 14 | $1.4 \times 10^{-0}$ |
| | 16 | $1.5 \times 10^{-0}$ |
| iso-amyl | 6 | $1.8 \times 10^{-0}$ |
| | 8 | $1.1 \times 10^{-0}$ |
| | 10 | $1.1 \times 10^{-0}$ |
| | 12 | $1.3 \times 10^{-0}$ |
| | 14 | $1.5 \times 10^{-0}$ |
| | 16 | $1.2 \times 10^{-0}$ |
| iso-propyl | 6 | $2.1 \times 10^{-0}$ |
| | 8 | $1.8 \times 10^{-0}$ |
| | 10 | $1.6 \times 10^{-0}$ |
| | 12 | $1.4 \times 10^{-0}$ |
| | 14 | $1.5 \times 10^{-0}$ |
| | 16 | $1.5 \times 10^{-0}$ |
| n-butyl | 6 | $2.3 \times 10^{-0}$ |
| | 8 | $1.7 \times 10^{-0}$ |
| | 10 | $1.7 \times 10^{-0}$ |
| | 12 | $1.5 \times 10^{-0}$ |

TABLE-continued

SURFACTANT PROPERTIES OF SODIUM SULFONATE DERIVATIVE

0.70 g/l surfactant
10.00 g/l NaCl  } Surfactant Test Solution
20.00 ml/l alcohol

| Alcohol | n-Alkane | IFT (dynes/cm) |
|---|---|---|
|  | 14 | $1.6 \times 10^{-0}$ |
|  | 16 | $1.2 \times 10^{-0}$ |

In a manner similar to that set forth in the above examples, coal may be treated with other mono- and polyhydric aromatic compounds such as hydroxy naphthalene or resorcinol in the presence of an acidic catalyst such as sulfuric acid or a Friedel Crafts catalyst such as aluminum chloride to obtain depolymerized products. These depolymerized products may then be sulfonated after the appropriate steps of recovery have been effected by treatment with a sulfonating agent such as sulfur trioxide or sulfuric acid and thereafter neutralized with a basic compound such as sodium hydroxide to obtain the sodium sulfonate derivative of the depolymerized products which may then exhibit surfactant properties similar in nature to those exhibited by the sodium sulfonated salt of the depolymerized product which was obtained in Example IV above.

I claim as my invention:

1. A process for the preparation of neutralized sulfonated derivatives of depolymerized coal as a surfactant which comprises treating the product obtained from the depolymerization of coal in the presence of a catalyst consisting essentially of a boron trifluoride etherate in a solvent comprising a mono- or polyhydroxy aromatic hydrocarbon with a sulfonating agent at sulfonation conditions, neutralizing the sulfonated product and recovering said neutralized sulfonated derivative of depolymerized coal surfactant.

2. The process as set forth in claim 1 in which said sulfonation conditions include a temperature in the range of from about ambient to about 50° C. and a pressure in the range of from about atmospheric to about 10 atmospheres.

3. The process as set forth in claim 1 in which the sulfonating agent is sulfur trioxide.

4. The process as set forth in claim 1 in which the sulfonating agent is sulfuric acid.

5. The process as set forth in claim 1 in which said monohydroxy aromatic compound is phenol.

6. The process as set forth in claim 1 in which said monohydroxy compound is hydroxynaphthalene.

7. The process as set forth in claim 1 in which said polyhydroxy aromatic compound is resorcinol.

* * * * *